United States Patent
Kontham et al.

(10) Patent No.: US 10,941,155 B2
(45) Date of Patent: Mar. 9, 2021

(54) FURO[2,3-B]PYRAN-2-ONE COMPOUNDS AND PROCESS FOR PREPARATION THEREOF

(71) Applicant: COUNCIL OF SCIENTIFIC & INDUSTRIAL RESEARCH, New Delhi (IN)

(72) Inventors: Ravindar Kontham, Pune (IN); Sagar Sudam Thorat, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/618,720

(22) PCT Filed: May 30, 2018

(86) PCT No.: PCT/IN2018/050345
§ 371 (c)(1),
(2) Date: Dec. 2, 2019

(87) PCT Pub. No.: WO2018/220647
PCT Pub. Date: Dec. 6, 2018

(65) Prior Publication Data
US 2020/0165263 A1    May 28, 2020

(30) Foreign Application Priority Data
May 30, 2017   (IN) .............................. 201711018894

(51) Int. Cl.
*C07D 493/04*   (2006.01)

(52) U.S. Cl.
CPC .................. *C07D 493/04* (2013.01)

(58) Field of Classification Search
CPC .................................................. C07D 493/04
See application file for complete search history.

(56) References Cited

PUBLICATIONS

Willis et al., (10) Synlett 1491-1493 (2003) (Year: 2003).*
Willis et al., One-pot Synthesis of Perhydrofuro [2,3-b]pyran Derivatives, Synlett 2003, No. 10, pp. 1491-1493.
Thorat et al., Synthesis of Furo[2,3-b]pyran-2-ones through Ag(I)— or Ag(I)—Au(I)—Catalyzed Cascade Annulation of Alkynols and α-Ketoesters, Org. Lett. 2018, 20, pp. 872-875.
International Search Report of International Application No. PCT/IN2018/050345.
Kambale et al., "Lewis acid catalyzed cascade annulation of alkynols with α-ketoesters: a facile access to γ-spiroketal-γ-lactones". Chem. Commun., 2017, 53, pp. 6641-6644.
Tang et al., "Lewis acid-mediated reactions of 1-cyclopropyl-2-arylethanone derivatives with diethyl 2-oxomalonate and ethyl 2-oxoacetate", Tetrahedron: 2009, 65 (45),pp. 9336-9343.
Li et al., "Lactols in an asymmetric aldol-desymmetrization sequence: access to tetrahydro—4H—furo[2,3-b]pyran—2—one and tetrahydro—4H—furo[2,3-b]furan—2—one derivatives", Org. Biomol. Chem., 2017.15, 1407-1417.
Li et al., "Bimetallic Gold(I)/Chiral N,N'—Dioxide Nickel(II) Asymmetric Relay Catalysis: Chemo-and Enantioselective Synthesis of Spiroketals and Spiroaminals", Angew.Chem.Int.Ed.; 2016, 55, pp. 6075-6078.
Ravindar et al., "A highly efficient access to spiroketals, monounsaturated spiroketals, and furans: Hg(II)-catalyzed cyclization of alkyne diols and triols". Org. Lett., 2011, 13 (12), pp. 3178-3181.
Wang et al., "Synthesis of spiroaminals and spiroketals with bimetallic relay catalysis". *Org. Lett.*, 2014, 16 (1). pp. 22-25.

* cited by examiner

*Primary Examiner* — Timothy R Rozof
(74) *Attorney, Agent, or Firm* — Blank Rome LLP

(57) ABSTRACT

The present invention discloses a novel furo[2,3-b]pyran-2-one compound of formula (I) and a single step process for the preparation of furo[2,3-b]pyran-2-ones using Lewis acid-promoted cascade annulation of alkynols and α-ketoesters.

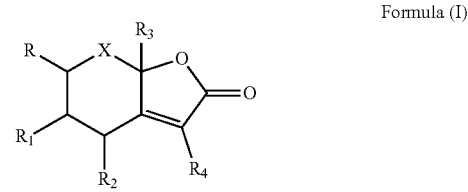

Formula (I)

8 Claims, 3 Drawing Sheets

FURO[2,3-B]PYRAN-2-ONE COMPOUNDS AND PROCESS FOR PREPARATION THEREOF

RELATED APPLICATIONS

This application is a national phase application of PCT/IN2018/050345, filed May 30, 2018, which claims priority to Indian Application No, 201711018894, filed May 30, 2017. The entire contents of those applications are incorporated herein by reference.

FIELD OF THE INVENTION

The present invention relates to novel furo[2,3-b]pyran-2-one compounds. More particularly, the present invention relates to novel furo[2,3-b]pyran-2-one compound of formula (I) and a single step process for the preparation of furo[2,3-b]pyran-2-ones using Lewis acid-promoted cascade annulation of alkynols and α-ketoesters.

BACKGROUND AND PRIOR ART OF THE INVENTION

Furo[2,3-b]pyrans are scaffolds found in a numerous biologically active natural products, including alboatrin (phytotoxic metabolite isolated from the culture filtrate of *Verticillium alboatrum*, which inhibits the root growth of the host plant (Maris Kabul) and causes vascular-wilt disease in alfalfa), xyloketals A-D & H (isolated from marine mangrove endophytic fungus from the South China Sea, which known to show strong calcium channel blocking activities and inhibitory activities of acetylcholine esterase), myxostiolide (plant growth regulator isolated from *Myxotrichum stipitatum*), hyperaspidinol (isolated from the leaves of *Hypericum chinense*, these plants have been used medicinally for treating illnesses such as hepatitis and depression, and as topical antimicrobials for wounds and snake bites), spicatolide-C (anti-inflammatory) and guaianolide (probable potential inhibitors of nitric oxide production in lipopolysaccharide-activated macrophage).

Article titled "Lewis acid catalyzed cascade annulation of alkynols with α-ketoesters: a facile access to γ-spiroketal-γ-lactones" by D A Kambale et al. published in *Chem. Commun.*, 2017, 53, pp 6641-6644 reports a novel Lewis acid catalyzed intermolecular cascade annulation of alkynols with α-ketoesters. This simple and efficient cascade annulation proceeds through a 5-exo-dig cyclization of alkynols followed by annulation with α-ketoester to provide a wide variety of unsaturated γ-spiroketal-γ-lactones (1,6-dioxaspiro[4.4]non-3-en-2-ones) related to many natural products.

Article titled "Lewis acid-mediated reactions of 1-cyclopropyl-2-arylethanone derivatives with diethyl 2-oxomalonate and ethyl 2-oxoacetate" by X Y Tang et al. published in *Tetrahedron;* 2009, 65 (45), pp 9336-9343 reports TMSOTf-mediated reactions of 2-aryl-1-(1-phenylcyclopropyl)ethanones 1 with diethyl 2-oxomalonate 2 afford a novel method for the synthesis of spiro-γ-lactone derivatives 3 in good to excellent yields via a sequential reaction involving a nucleophilic ring-opening reaction of the cyclopropane by $H_2O$, an aldol-type reaction and a cyclic transesterification mediated by Lewis acid. On the other hand, we found that TMSOTf-mediated reactions of 1-cyclopropyl-2-arylethanones with ethyl 2-oxoacetate could also provide the corresponding spiro-γ-lactone derivatives in moderate yields along with another spiro-γ-lactone derivative derived from the reaction of with two molecules of ethyl 2-oxoacetate.

Article titled "Bimetallic Gold(I)/Chiral N,N'-Dioxide Nickel(II) Asymmetric Relay Catalysis: Chemo- and Enantioselective Synthesis of Spiroketals and Spiroaminals" by J Li et al. published in *Angew. Chem. Int. Ed.;* 2016, 55, pp 6075-6078 reports a highly efficient asymmetric cascade reaction between keto esters and alkynyl alcohols and amides. The success of the reaction was attributed to the combination of chiral Lewis acid N,N'-dioxide nickel(II) catalysis with achiral π-acid gold(I) catalysis working as an asymmetric relay catalytic system. The corresponding spiroketals and spiroaminals were synthesized in up to 99% yield, 19:1 d.r., and more than 99% ee under mild reaction conditions. Control experiments suggest that the N,N'-dioxide ligand was essential for the formation of the spiro products.

Article titled "A highly efficient access to spiroketals, mono-unsaturated spiroketals, and furans: Hg(II)-catalyzed cyclization of alkyne diols and triols" by K Ravindar et al. published in *Org. Lett.*, 2011, 13 (12), pp 3178-3181 reports Hg(II) salts are identified as highly efficient catalysts for the versatile construction of spiroketals from alkyne diols in aqueous conditions. Monounsaturated spiroketals and furans were accessed with equal ease when propargylic triols (or propargylic diols) were subjected to similar conditions. Even the semiprotected alkyne diols gave the corresponding spiroketals with the same ease in a cascade manner. The reactions are instant and high yielding at ambient temperatures.

Article titled "Synthesis of spiroaminals and spiroketals with bimetallic relay catalysis" by X Wang et al. published in *Org. Lett.*, 2014, 16 (1), pp 22-25 reports a novel tandem metal relay catalytic system was developed by combining gold-catalyzed cycloisomerization with an early transition-metal-catalyzed inverse-electron-demand hetero-Diels-Alder (IED-HDA) reaction. Various biologically important spiroaminals and spiroketals were obtained with very high efficiency under mild conditions.

Article titled "Lactols in an asymmetric aldol-desymmetrization sequence: access to tetrahydro-4H-furo[2,3-b]pyran-2-one and tetrahydro-4H-furo[2,3-b]furan-2-one derivatives" by J Y Li et al. published in *Org. Biomol. Chem.*, 2017, 15, 1407-1417 reports an asymmetric aldol-desymmetrization sequence which provided highly efficient access to important bicyclic oxygen-containing scaffolds with multiple chiral centers and one is a quaternary stereogenic center containing a free hydroxy group. Moreover, starting from racemic precursors, the final products were obtained as two separable diastereomers by flash chromatography.

Despite their potential biological properties, only a few synthetic methods have been documented in the literature. For instance, $TiCl_4$ mediated addition of 3,4-dihydro-2H-pyran to (2-trimethylsilyl)ethyl pyruvate, results in perhydro [2,3-b]pyran derivative, and the Schmidt's cascade cyclization of 3,4-dihydro-2H-pyran with oxalyl chloride, gives the 2-chloro variant in MeOH at elevated temperature of 120° C. in 42% yield. All these approaches had several limitations such as usage of precyclized starting materials, elevated temperatures and limited substrate scope.

Therefore, there is a need to develop novel furo[2,3-b]pyran-2-one compounds, a simple process for preparation and composition of furo[2,3-b]pyran-2-one compounds thereof having biological activity.

OBJECTIVE OF THE INVENTION

The main objective of the present invention is to provide a furo[2,3-b]pyran-2-one compound of formula (I).

Another objective of the present invention is to provide a single step process for the preparation of furo[2,3-b]pyran-2-one compound of formula (I).

Yet another objective of the present invention is to provide a composition comprising the furo[2,3-b]pyran-2-ones compounds having biological activity.

SUMMARY OF THE INVENTION

Accordingly, the present invention provides a furo[2,3-b]pyran-2-one compound of formula (I),

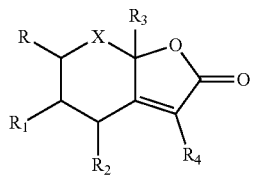

Formula (I)

wherein, R, $R_1$, and $R_2$ are independently selected from the group consisting of hydrogen, $C_1$-$C_6$ alkyl and $C_1$-$C_6$ cycloalkyl;
$R_3$ is selected from the group consisting of hydrogen, $C_1$-$C_7$ alkyl and $C_6$ aryl;
$R_4$ is selected from the group consisting of hydrogen, $C_1$-$C_7$ alkyl, $C_4$-$C_8$ aryl, $C_4$-$C_8$ hetero aryl, alkynyl, substituted alkynyl, alkenyl and substituted alkenyl; and
X is selected from the group consisting of O, NH and S.

In preferred embodiment, the compound of formula (I) is selected from the group consisting of 3',7a'-Dimethyl-4'H,6'H-spiro[cyclohexane-1,5'-furo[2,3-b]pyran]-2'(7a'H) one (5aa), 7a'-Methyl-3'-phenyl-4'H,6'H-spiro[cyclohexane-1,5'-furo[2,3-b]pyran]-2'(7a'H)-one (5ab), 3'-(4-Methoxyphenyl)-7a'-methyl-4'H,6'H-spiro[cyclohexane-1,5'-furo[2,3-b]pyran]-2'(7a'H)-one (5ac), 7a'-Methyl-3'-(4-nitrophenyl)-4'H,6'H-spiro[cyclohexane-1,5'-furo[2,3-b]pyran]-2'(7a'H)-one (5ad), 7a'-Benzyl-3'-methyl-4'H,6'H-spiro[cyclohexane-1,5'-furo[2,3-b]pyran]-2'(7a'H)-one (5ba), 3',7a'-Dimethyl-4'H,6'H-spiro[cyclopentane-1,5'-furo[2,3-b]pyran]-2'(7a'H)-one (5ca), 7a'-Methyl-3'-(1-methyl-1H-indol-3-yl)-4'H,6'H-spiro[cyclopentane-1,5'-furo[2,3-b]pyran]-2'(7a'H)-one (5cg), 3,7a-Dimethyl-5,6-dihydro-4H-furo[2,3-b]pyran-2(7aH)-one (5da), 7a-Methyl-3-phenyl-5,6-dihydro-4H-furo[2,3-b]pyran-2(7aH)-one (5db), 3-(4-Methoxyphenyl)-7a-methyl-5,6-dihydro-4H-furo[2,3-b]pyran-2(7aH)-one (5dc), 7a-Methyl-3-(4-nitrophenyl)-5,6-dihydro-4H-furo[2,3-b]pyran-2(7aH)-one (5dd), 7a-Methyl-3-(phenylethynyl)-5,6-dihydro-4H-furo[2,3-b]pyran-2(7aH)-one (5de), (E)-7a-Methyl-3-styryl-5,6-dihydro-4H-furo[2,3-b]pyran-2(7aH)-one (5df), 7a-Methyl-3-(1-methyl-1H-indol-3-yl)-5,6-dihydro-4H-furo[2,3-b]pyran-2(7aH)-one (5dg), 7a-Methyl-3-(thiophen-2-yl)-5,6-dihydro-4H-furo[2,3-b]pyran-2(7aH)-one (5dh), 4a,7-Dimethyl-2,3-dihydrofuro[2,3-b][1,4]dioxin-6(4aH)-one (5ea), 3,6,7a-Trimethyl-5,6-dihydro-4H-furo[2,3-b]pyran-2(7aH)-one (5fa), 3,6,6,7a-Tetramethyl-5,6-dihydro-4H-furo[2,3-b]pyran-2(7aH)-one (5ga), 3-(4-Methoxyphenyl)-6,6,7a-trimethyl-5,6-dihydro-4H-furo[2,3-b]pyran-2(7aH)-one (5gc) and 6,6,7a-Trimethyl-3-(thiophen-2-yl)-5,6-dihydro-4H-furo[2,3-b]pyran-2(7aH)-one (5gh).

In one embodiment of the present invention, the present invention provides a single step process for synthesis of furo[2,3-b]pyran-2-one compound of formula (I), comprising the step of reacting an alkynol of formula (III) and an α-ketoester of formula (II) in presence of a Lewis acid catalyst to obtain the corresponding furo[2,3-b]pyran-2-one compound of formula (I).

In an embodiment, the alkynol of formula (III) is;

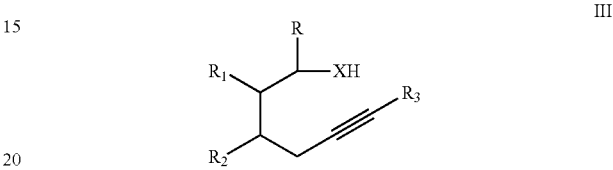

wherein, R, $R_1$, and $R_2$ are independently selected from the group consisting of hydrogen, $C_1$-$C_6$ alkyl and $C_1$-$C_6$ cycloalkyl;
$R_3$ is selected from the group consisting of hydrogen and $C_6$ aryl; and
X is selected from the group consisting of O, NH and S.

In preferred embodiment, the alkynol is selected from the group consisting of (1-(but-3-yn-1-yl)cyclohexyl)methanol (4a), (1-(4-phenylbut-3-yn-1-yl)cyclohexyl)methanol (4b), (1-(but-3-yn-1-yl)cyclopentyl)methanol (4c), 5-hexyne-1-ol (4d), 2-(prop-2-yn-1-yloxy)ethan-1-ol (4e), hept-6-yn-2-ol (4f) and 2-methylhept-6-yn-2-ol (4g).

In an embodiment, the α-ketoester of formula (II) is;

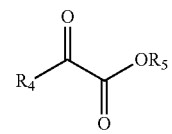

wherein, $R_4$ is selected from the group consisting of hydrogen, $C_1$-$C_7$ alkyl, $C_4$-$C_8$ aryl, $C_4$-$C_8$ hetero aryl, alkynyl, substituted alkynyl, alkenyl and substituted alkenyl; and
$R_5$ is selected from the group consisting of $C_2$-$C_4$ alkyl.

In preferred embodiment, the α-ketoester is selected from the group consisting of ethyl pyruvate (2a), ethyl phenylglyoxylate (2b), ethyl anisylglyoxylate (2c), ethyl p-nitrophenyglyoxylate (2d), ethyl 2-oxo-4-phenylbut-3-ynoate (2e), ethyl (E)-2-oxo-4-phenylbut-3-enoate (2f), tert-butyl indoleglyoxylate (2g) and ethyl thiophene glyoxylate (2h).

The Lewis acid catalyst is selected from the group consisting of $Hg(OTf)_2$, AgOTf, $Bi(OTf)_3$, $In(OTf)_3$, $BF_3OEt_2$/$Bi(OTf)_3$, TFA/$(BiOTf)_3$, AgOTf/$PPh_3PAuCl$, $Cu(OTf)_2$, $Sc(OTf)_3$, $Bi(OTf)_3$, $Bi(OTf)_3$ and $FeCl_3$ or mixture thereof.

In preferred embodiment of the present invention, the process is carried out at temperature in the range of 25 to 100° C. for the period in the range of 4 to 12 hrs.

DETAILED DESCRIPTION OF THE INVENTION

Figure 1:
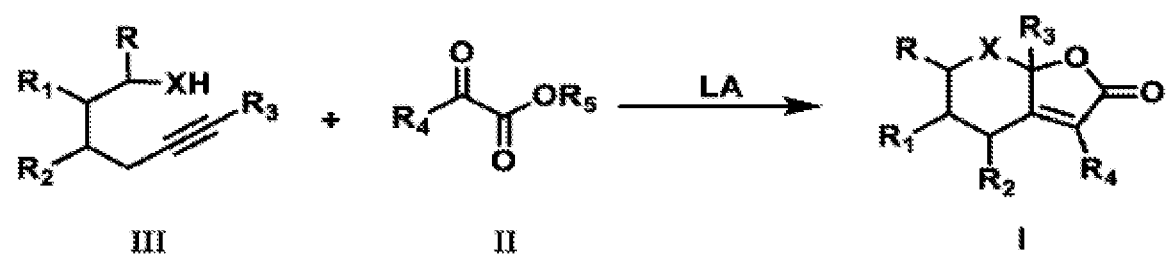
FIG. 1 shows the single step process for preparation of furo[2,3-b]pyran-2-one compound of formula (I).

The invention will now be described in detail in connection with certain preferred and optional embodiments, so that various aspects thereof may be more fully understood and appreciated.

In view of above, the present invention provides novel furo[2,3-b]pyran-2-ones compounds and a one step process for preparation using a Lewis acid-promoted cascade annulation of alkynols and α-ketoesters to give furo[2,3-b]pyran-2-ones in high yields.

In an embodiment, the present invention provides a furo[2,3-b]pyran-2-one compound of formula (I),

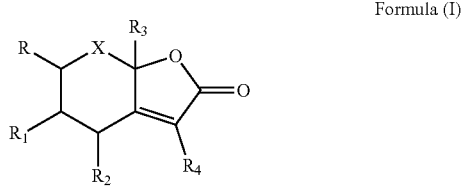

Formula (I)

wherein, R, $R_1$, and $R_2$ are independently selected from the group consisting of hydrogen, $C_1$-$C_6$ alkyl and $C_1$-$C_6$ cycloalkyl;
$R_3$ is selected from the group consisting of hydrogen, $C_1$-$C_7$ alkyl and $C_6$ aryl;
$R_4$ is selected from the group consisting of hydrogen, $C_1$-$C_7$ alkyl, $C_4$-$C_8$ aryl, $C_4$-$C_8$ hetero aryl, alkynyl, substituted alkynyl, alkenyl and substituted alkenyl; and
X is selected from the group consisting of O, NH and S.

In preferred embodiment, the compound of formula (I) is selected from the group consisting of
3',7a'-Dimethyl-4'H,6'H-spiro[cyclohexane-1,5'-furo[2,3-b]pyran]-2'(7a'H) one (5aa),
7a'-Methyl-3'-phenyl-4'H,6'H-spiro[cyclohexane-1,5'-furo[2,3-b]pyran]-2'(7a'H)-one (5ab),
3'-(4-Methoxyphenyl)-7a'-methyl-4'H,6'H-spiro[cyclohexane-1,5'-furo[2,3-b]pyran]-2'(7a'H)-one (5ac),
7a'-Methyl-3'-(4-nitrophenyl)-4'H,6'H-spiro[cyclohexane-1,5'-furo[2,3-b]pyran]-2'(7a'H)-one (5ad),
7a'-Benzyl-3'-methyl-4'H,6'H-spiro[cyclohexane-1,5'-furo[2,3-b]pyran]-2'(7a'H)-one (5ba),
3',7a'-Dimethyl-4'H,6'H-spiro[cyclopentane-1,5'-furo[2,3-b]pyran]-2'(7a'H)-one (5ca),
7a'-Methyl-3'-(1-methyl-1H-indol-3-yl)-4'H,6'H-spiro[cyclopentane-1,5'-furo[2,3-b]pyran]-2'(7a'H)-one (5cg),
3,7a-Dimethyl-5,6-dihydro-4H-furo[2,3-b]pyran-2(7aH)-one (5da),
7a-Methyl-3-phenyl-5,6-dihydro-4H-furo[2,3-b]pyran-2(7aH)-one (5db),
3-(4-Methoxyphenyl)-7a-methyl-5,6-dihydro-4H-furo[2,3-b]pyran-2(7aH)-one (5dc),
7a-Methyl-3-(4-nitrophenyl)-5,6-dihydro-4H-furo[2,3-b]pyran-2(7aH)-one (5dd),
7a-Methyl-3-(phenylethynyl)-5,6-dihydro-4H-furo[2,3-b]pyran-2(7aH)-one (5de),
(E)-7a-Methyl-3-styryl-5,6-dihydro-4H-furo[2,3-b]pyran-2(7aH)-one (5df),
7a-Methyl-3-(1-methyl-1H-indol-3-yl)-5,6-dihydro-4H-furo[2,3-b]pyran-2(7aH)-one (5dg),
7a-Methyl-3-(thiophen-2-yl)-5,6-dihydro-4H-furo[2,3-b]pyran-2(7aH)-one (5dh),
4a,7-Dimethyl-2,3-dihydrofuro[2,3-b][1,4]dioxin-6(4aH)-one (5ea),
3,6,7a-Trimethyl-5,6-dihydro-4H-furo[2,3-b]pyran-2(7aH)-one (5fa),
3,6,6,7a-Tetramethyl-5,6-dihydro-4H-furo[2,3-b]pyran-2(7aH)-one (5ga),
3-(4-Methoxyphenyl)-6,6,7a-trimethyl-5,6-dihydro-4H-furo[2,3-b]pyran-2(7aH)-one (5gc), and
6,6,7a-Trimethyl-3-(thiophen-2-yl)-5,6-dihydro-4H-furo[2,3-b]pyran-2(7aH)-one (5gh).

In one embodiment, the present invention provides a single step process for preparation of furo[2,3-b]pyran-2-one compound of formula (I), comprising reacting an alkynol of formula (III) and an α-ketoester of formula (II) in presence of a Lewis acid catalyst to obtain the corresponding furo[2,3-b]pyran-2-one compound of formula (I).

In preferred embodiment of the present invention, the process is carried out at temperature in the range of 25 to 100° C. for the period in the range of 4 to 12 hrs.

The single step process for preparation of furo[2,3-b]pyran-2-one compound of formula (I) is shown below in FIG. 1, which is reproduced below as scheme 1:

Scheme: 1

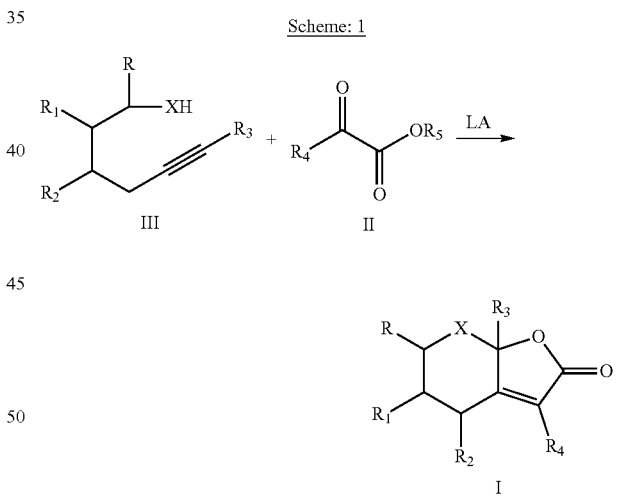

wherein, R, $R_1$, and $R_2$ are independently selected from the group consisting of hydrogen, $C_1$-$C_6$ alkyl and $C_1$-$C_6$ cycloalkyl;
$R_3$ is selected from the group consisting of hydrogen, $C_1$-$C_7$ alkyl and $C_6$ aryl;
$R_4$ is selected from the group consisting of hydrogen, $C_1$-$C_7$ alkyl, $C_4$-$C_8$ aryl, $C_4$-$C_8$ hetero aryl, alkynyl, substituted alkynyl, alkenyl and substituted alkenyl;
$R_5$ is selected from the group consisting of $C_2$-$C_4$ alkyl;
X is selected from the group consisting of O, NH and S; and
LA is Lewis Acid.

In an embodiment, the alkynol of formula (III) is;

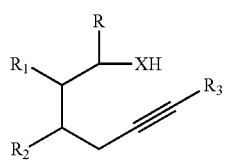

wherein, R, $R_1$, and $R_2$ are independently selected from the group consisting of hydrogen, $C_1$-$C_6$ alkyl and $C_1$-$C_6$ cycloalkyl;

$R_3$ is selected from the group consisting of hydrogen and $C_6$ aryl;

X is selected from the group consisting of O, NH and S.

In preferred embodiment, the alkynol is selected from the group consisting of (1-(but-3-yn-1-yl)cyclohexyl)methanol (4a), (1-(4-phenylbut-3-yn-1-yl)cyclohexyl)methanol (4b), (1-(but-3-yn-1-yl)cyclopentyl)methanol (4c), 5-hexyne-1-ol (4d), 2-(prop-2-yn-1-yloxy)ethan-1-ol (4e), hept-6-yn-2-ol (4f) and 2-methylhept-6-yn-2-ol (4g).

In another embodiment, the α-ketoester of formula (II) is;

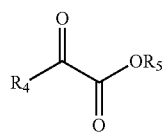

wherein, $R_4$ is selected from the group consisting of hydrogen, $C_1$-$C_7$ alkyl, $C_4$-$C_8$ aryl, $C_4$-$C_8$ hetero aryl, alkynyl, substituted alkynyl, alkenyl and substituted alkenyl; and $R_5$ is selected from the group consisting of $C_2$-$C_4$ alkyl.

In preferred embodiment, the α-ketoester is selected from the group consisting of ethyl pyruvate (2a), ethyl phenylglyoxylate (2b), ethyl anisylglyoxylate (2c), ethyl p-nitrophenyglyoxylate (2d), ethyl 2-oxo-4-phenylbut-3-ynoate (2e), ethyl (E)-2-oxo-4-phenylbut-3-enoate (2f), tert-butyl indoleglyoxylate (2g) and ethyl thiophene glyoxylate (2h).

The Lewis acid catalyst is selected from the group consisting of $Hg(OTf)_2$, AgOTf, $Bi(OTf)_3$, $In(OTf)_3$, $BF_3OEt_2$/$Bi(OTf)_3$, TFA/$(BiOTf)_3$, AgOTf/$PPh_3PAuCl$, $Cu(OTf)_2$, $Sc(OTf)_3$, $Bi(OTf)_3$, $Bi(OTf)_3$ and $FeCl_3$ or mixture thereof.

In an embodiment of the present invention, there is provided a single step process for preparation of furo[2,3-b]pyran-2-one compound of formula (I) as claimed in claim 1, comprising the step of reacting an alkynol of formula (III)

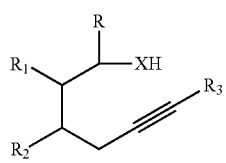

wherein, R, $R_1$ and $R_2$ are independently selected from the group consisting of hydrogen, $C_1$-$C_6$ alkyl and $C_1$-$C_6$ cycloalkyl;

$R_3$ is selected from the group consisting of hydrogen and $C_6$ aryl; and

X is selected from the group consisting of O, NH and S.

and an α-ketoester of formula (II)

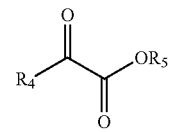

wherein, $R_4$ is selected from the group consisting of hydrogen, $C_1$-$C_7$ alkyl, $C_4$-$C_8$ aryl, $C_4$-$C_8$ hetero aryl, alkynyl, substituted alkynyl, alkenyl, and substituted alkenyl; and $R_5$ is selected from the group consisting of $C_2$-$C_4$ alkyl;

in presence of a Lewis acid catalyst to obtain the corresponding furo[2,3-b]pyran-2-one compound of formula (I).

The annulation of cyclohexane fused alkynol with ethyl pyruvate, ethyl phenylglyoxylate, ethyl anisylglyoxylate and ethyl 4-nitrophenylglyoxylate gives the corresponding adducts 5aa-ad in good yields. Cyclohexane fused internal alkynol with ethyl pyruvate provided 5ba in good yield of 59%. A cyclopentane fused terminal alkynol participated well in the reaction with ethyl pyruvate and indole derived α-ketoester to give 5ca and 5cg in good yields. Commercially available 5-hexyn-1-ol also proved to be a good substrate in this process delivering various adducts 5da-dd, along with very interesting indole and thiophene derived analogs 5dg and 5dh in good yields. The phenyl acetylene derived α-ketoester is also a good substrate for this transformation and afforded 5de in 54% yield.

Figure 2:
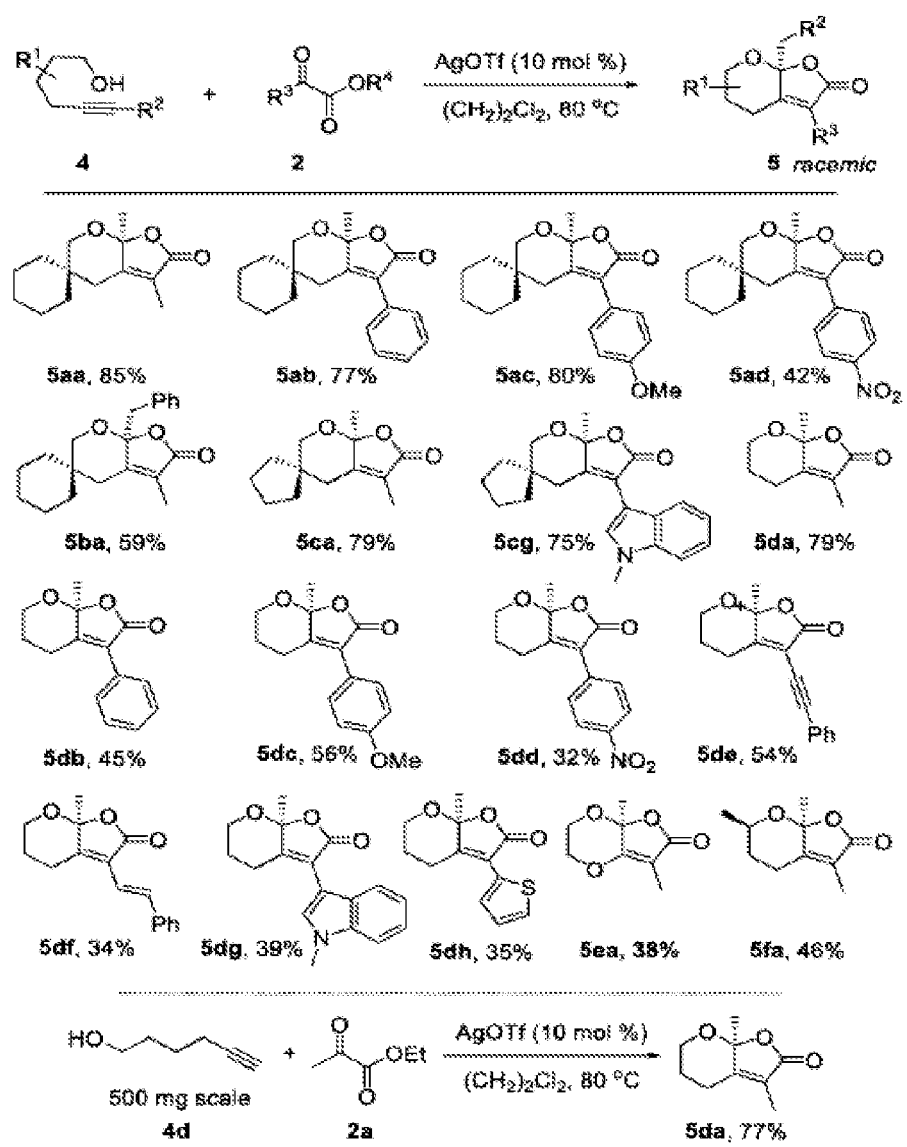
FIG. 2 shows the process for preparation of synthesis of furo[2,3-b]pyran-2-ones using primary and secondary alkynols and furo[2,3-b]pyran-2-one compounds of formula (I).

The process for preparation of synthesis of furo[2,3-b]pyran-2-ones using primary and secondary alkynols and furo[2,3-b]pyran-2-one compounds of formula (I) is shown in FIG. 2.

Figure 3:
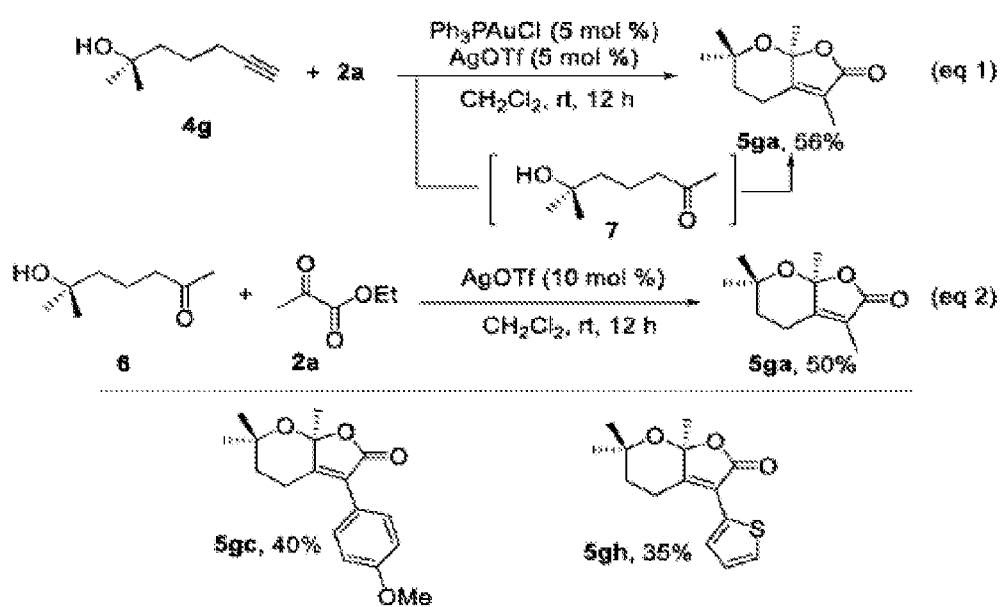
FIG. 3 shows the process for the synthesis of furo[2,3-b]pyran-2-ones using tertiary alkynols.

The process for the synthesis of furo[2,3-b]pyran-2-ones using tertiary alkynols is shown in FIG. 3.

The compounds of formula (I) shows high biological activity like phytotoxic metabolite activity, calcium channel blockers, anti-inflammatory or inhibitor of nitric oxide production.

In yet another embodiment, a pharmaceutical composition is provided comprising a compound of formula (I), or a stereoisomer, or ester or pharmaceutically acceptable salt thereof, and a pharmaceutically acceptable carrier, diluent or excipient.

The compounds of the present invention possess antibacterial activity against a wide spectrum of Gram-positive and Gram-negative bacteria, aerobic and anaerobic organisms such as *Staphylococcus, Lactobacillus, Streptococcus, Escherichia, Enterobacter, Pseudomonas, Proteus, Citrobacter, Baccillus, Clostridium, Salmonella*, and other organisms. Also, the compounds of the present invention possess antibacterial activity against bacterial species resistant to conventional [beta]-lactams, such as MRSA. Further, the compounds of the instant invention are effective as antiplasmodium agent for the treatment of malaria and anti-Alzheimer's. The compound of formula (I) disclosed herein is present in the composition in an amount which is effective to treat the disease or the condition caused by the bacterial strains mentioned above.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres.

In another embodiment, the present invention relates to administering 'an effective amount' of the 'composition of invention' to the subject suffering from said disease. Accordingly, compound of formula I and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

The term "pharmaceutically acceptable" means that which is useful in preparing a pharmaceutical composition that is generally non-toxic and is not biologically undesirable and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The following examples, which include preferred embodiments, will serve to illustrate the practice of this invention, it being understood that the particulars shown are by way of examples and for purpose of illustrative discussion of preferred embodiments of the invention only and are not limiting the scope of the invention.

EXAMPLES

Following examples are given by way of illustration therefore should not be construed to limit the scope of the invention.

Example A

General Procedure for the Synthesis of Furo[2,3-b]pyran-2-ones from Alkynols (Primary & Secondary) and α-ketoesters

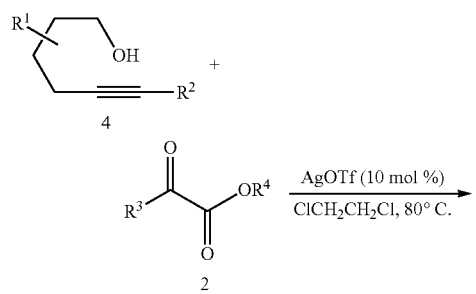

-continued

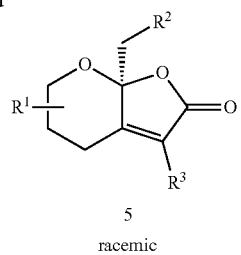

5
racemic

To the alkynol (4) (1.02 mmol) and α-ketoester (2) (1.02 mmol) in 3 mL of anhydrous $(CH_2)_2Cl_2$ in a dry round bottom flask, was added AgOTf (0.1 mmol) under argon atmosphere at 27° C. and the reaction mixture was stirred at 80° C. for 4 h. After completion of the reaction (monitored by TLC, visualized using UV, anisaldehyde, and $KMnO_4$ staining solutions), the reaction mixture was quenched with saturated aqueous solution of sodium bicarbonate ($NaHCO_3$) then extracted with $CH_2Cl_2$ (2×5 mL). The combined organic layers were dried over anhydrous sodium sulphate ($Na_2SO_4$) and filtered through sintered glass funnel. The residue was concentrated under reduced pressure and purified by silica gel column chromatography (100-200 mesh) to afford the corresponding furo[2,3-b]pyran-2-one (5).

Example B

General Procedure for the Synthesis of Furo[2,3-b]pyran-2-ones from Alkynols (Tertiary) and α-ketoesters

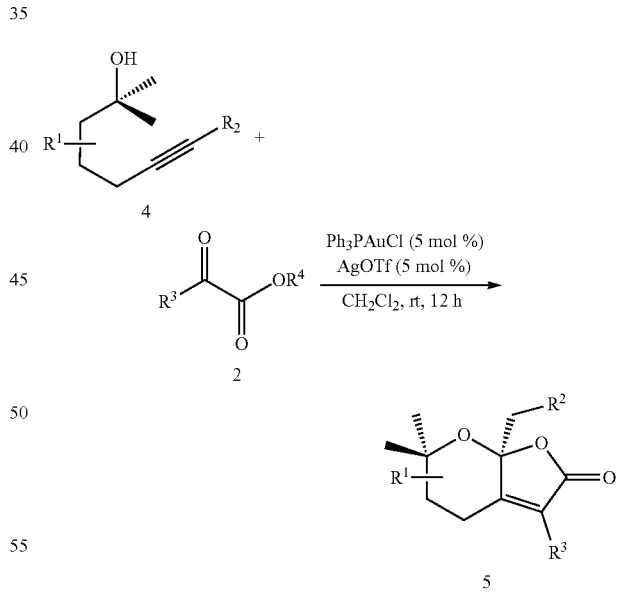

To the alkynol (4) (0.39 mmol) and α-ketoester (2) (0.39 mmol) in 3 mL of anhydrous $CH_2Cl_2$ in a dry round bottom flask, was added $PPh_3AuCl$ 0.02 mmol) under argon atmosphere at 27° C. and stirred the reaction mixture for 30 min and then AgOTf (0.02 mmol) was added and stirred reaction mixture at 27° C. After completion of the reaction (typically after 12 h, monitored by TLC, visualized using UV, anisaldehyde, and $KMnO_4$ staining solutions), the reaction mixture was quenched with saturated aqueous solution of sodium bicarbonate (NaHCO₃) then extracted with CH₂Cl₂ (2×5 mL). The combined organic layers were dried over anhydrous sodium sulphate (Na₂SO₄) and filtered through sintered glass funnel. The residue was concentrated under reduced pressure and purified by silica gel column chromatography (100-200 mesh) to afford the corresponding furo[2,3-b]pyran-2-one (5).

Example 1

3',7a'-Dimethyl-4'H,6'H-spiro[cyclohexane-1,5'-furo[2,3-b]pyran]-2'(7a'H) one (5aa)

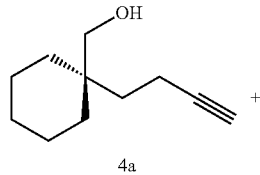

4a

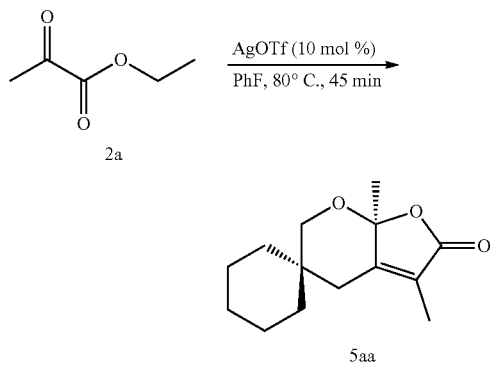

To the mixture of (1-(but-3-yn-1-yl)cyclohexyl)methanol (4a) (0.05 g, 0.3 mmol), ethyl pyruvate (2a) (0.034 g, 0.3 mmol) in anhydrous fluorobenzene (PhF) (3 mL) was added AgOTf (0.007 g, 0.03 mmol) at 27° C. under argon atmosphere and stirred the reaction mixture for 45 min at 80° C. After completion of the reaction, the reaction mixture was quenched with saturated aqueous solution of sodium bicarbonate, and then extracted with EtOAc (2×5 mL). The combined organic layers were dried over anhydrous sodium sulphate (Na₂SO₄) and filtered through sintered glass funnel. The residue was concentrated under reduced pressure and purified by silica gel column chromatography (100-200 mesh) to afforded 3',7a'-dimethyl-4'H-spiro[cyclohexane-1,5'-furo[2,3-b]pyran]-2'(7a'H)-one (5aa) (0.059 g, 83%). TLC: R$_f$=0.45 (SiO₂, 20% EtOAc/hexanes). (0.121 g, 85%). TLC: R$_f$=0.45 (SiO₂, 20% EtOAc/hexanes); ¹H NMR (CDCl₃, 200 MHz): δ 3.69 (dd, J=12.2, 2.0 Hz, 1H), 3.49 (d, J=12.2 Hz, 1H), 2.77 (dd, J=13.5, 2.1 Hz, 1H), 2.09 (dd, J=13.5, 1.5 Hz, 1H), 1.81 (d, J=1.4 Hz, 3H), 1.59 (s, 3H), 1.55-1.30 (m, 10H); ¹³C NMR (CDCl₃, 50 MHz): δ 171.7, 159.0, 122.8, 104.8, 72.7, 38.8, 35.8, 33.8, 31.5, 26.1, 21.6, 21.5, 19.6, 8.1; HRMS (ESI): calcd for C₁₄H₂₁O₃ [M+H]⁺ 237.1485, found 237.1486.

Example 2

7a'-Methyl-3'-phenyl-4'H,6'H-spiro[cyclohexane-1,5'-furo[2,3-b]pyran]-2'(7a'H)-one (5ab)

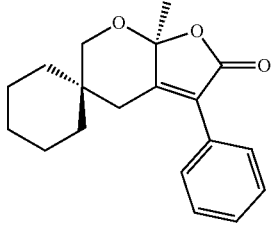

5ab

Following the General Procedure (A), to the mixture of (1-(but-3-yn-1-yl)cyclohexyl)methanol (4a) (0.1 g, 0.6 mmol), ethyl phenylglyoxylate (2b) (0.106 g, 0.6 mmol) in anhydrous (CH₂)₂Cl₂ (3 mL) was added AgOTf (0.015 g, 0.06 mmol) under argon atmosphere at 27° C. and stirred the reaction mixture for 4 h at 80° C. Purification of the crude product by column chromatography (SiO₂, 5% EtOAc/hexanes) afforded 7a'-methyl-3'-phenyl-4'H,6'H-spiro[cyclohexane-1,5'-furo[2,3-b]pyran]-2'(7a'H)-one (5ab) (0.138 g, 77%). TLC: R$_f$=0.4 (SiO₂, 20% EtOAc/hexanes); ¹H NMR (CDCl₃, 400 MHz): δ 7.53-7.36 (m, 5H), 3.78 (d, J=12.2 Hz, 1H), 3.56 (d, J=12.2 Hz, 1H), 3.00 (d, J=13.4 Hz, 1H), 2.30 (d, J=13.4 Hz, 1H), 1.73 (s, 3H), 1.52-1.26 (m, 10H); ¹³C NMR (CDCl₃, 101 MHz): δ 169.6, 160.01, 129.3, 129.0, 128.8, 128.7, 126.9, 126.5, 104.3, 72.2, 39.2, 35.9, 34.9, 35.7, 31.6, 25.9, 21.6, 21.2, 20.2; HRMS (ESI): calcd for C₁₉H₂₃O₃ [M+H]⁺ 299.1642, found 299.1643.

Example 3

3'-(4-Methoxyphenyl)-7a'-methyl-4'H,6'H-spiro[cyclohexane-1,5'-furo[2,3-b]pyran]-2'(7a'H)-one (5ac)

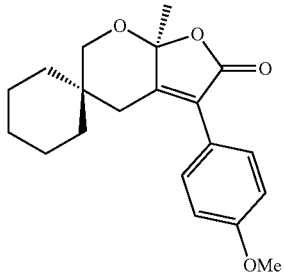

5ac

Following the General Procedure (A), to the mixture of (1-(but-3-yn-1-yl)cyclohexyl)methanol (4a) (0.1 g, 0.6 mmol), ethyl anisylglyoxylate (2c) (0.124 g, 0.6 mmol) in anhydrous (CH₂)₂Cl₂ (3 mL) was added AgOTf (0.015 g, 0.06 mmol) under argon atmosphere at 27° C. and stirred the reaction mixture for 4 h at 80° C. Purification of the crude product by column chromatography (SiO₂, 5% EtOAc/hexanes) afforded 3'-(4-methoxyphenyl)-7a'-methyl-4'H,6'H-spiro[cyclohexane-1,5'-furo[2,3-b]pyran]-2'(7a'H)-one (5ac) (0.158 g, 80%). TLC: R$_f$=0.4 (SiO₂, 20% EtOAc/hexanes); ¹H NMR (CDCl₃, 500 MHz): δ 7.44 (d, J=7.2 Hz, 2H), 6.96 (d, J=7.2 Hz, 2H), 3.84 (s, 3H), 3.75 (d, J=12.2 Hz, 1H), 3.55 (d, J=12.2 Hz, 1H), 3.0 (d, J=13.4 Hz, 1H), 2.28 (d, J=13.4 Hz, 1H), 1.71 (s, 3H), 1.48-1.28 (m, 10H); $^{13}$C NMR (CDCl$_3$, 126 MHz): δ 169.9, 159.9, 158.4, 130.1, 126.4, 121.4, 114.1, 104.3, 72.2, 55.3, 39.0, 35.9, 34.8, 31.7, 25.9, 21.7, 21.2, 20.3; HRMS (ESI): calcd for C$_{20}$H$_{25}$O$_4$ [M+H]$^+$ 329.1747, found 329.1749.

Example 4

7a'-Methyl-3'-(4-nitrophenyl)-4'H,6'H-spiro[cyclohexane-1,5'-furo[2,3-b]pyran]-2'(7a'H)-one (5ad)

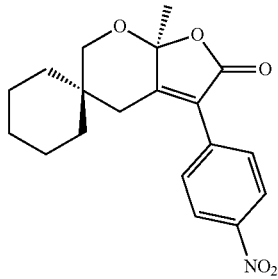

5ad

Following the General Procedure (A), to the mixture of (1-(but-3-yn-1-yl)cyclohexyl)methanol (4a) (0.1 g, 0.6 mmol), ethyl p-nitrophenylglyoxylate (2d) (0.133 g, 0.6 mmol) in anhydrous (CH$_2$)$_2$Cl$_2$ (3 mL) was added AgOTf (0.015 g, 0.06 mmol) under argon atmosphere at 27° C. and stirred the reaction mixture for 4 h at 80° C. Purification of the crude product by column chromatography (SiO$_2$, 10% EtOAc/hexanes) afforded 7a'-methyl-3'-(4-nitrophenyl)-4'H,6'H-spiro[cyclohexane-1,5'-furo[2,3-b]pyran]-2'(7a'H)-one (5ad) (0.087 g, 42%). TLC: R$_f$=0.2 (SiO$_2$, 20% EtOAc/hexanes); $^1$H NMR (CDCl$_3$, 400 MHz): δ 8.32 (d, J=8.5 Hz, 2H), 7.69 (d, J=8.5 Hz, 2H), 3.80 (d, J=12.8 Hz, 1H), 3.60 (d, J=12.2 Hz, 1H), 2.98 (d, J=13.4 Hz, 1H), 2.40 (d, J=14.0 Hz, 1H), 1.76 (s, 3H), 1.48-1.29 (m, 10H); $^{13}$C NMR (CDCl$_3$, 101 MHz): δ 168.6, 163.2, 147.8, 135.5, 129.8, 125.2, 123.9, 104.6, 72.1, 39.7, 35.9, 35.2, 31.6, 25.8, 21.6, 21.2, 20.0; HRMS (ESI): calcd for C$_{19}$H$_{22}$O$_5$N [M+H]$^+$ 344.1492, found 344.1494.

Example 5

7a'-Benzyl-3'-methyl-4'H,6'H-spiro[cyclohexane-1,5'-furo[2,3-b]pyran]-2'(7a'H)-one (5ba)

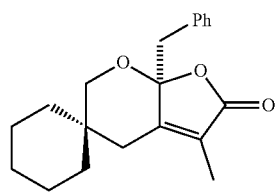

5ba

Following the General Procedure (A), to the mixture of (1-(4-phenylbut-3-yn-1-yl)cyclohexyl)methanol (4b) (0.05 g, 0.21 mmol), ethyl pyruvate (2a) (0.024 g, 0.21 mmol) in anhydrous (CH$_2$)$_2$Cl$_2$ (3 mL) was added AgOTf (0.005 g, 0.02 mmol) under argon atmosphere at 27° C. and stirred the reaction mixture for 4 h at 80° C. Purification of the crude product by column chromatography (SiO$_2$, 4% EtOAc/hexanes) afforded 7a'-benzyl-3'-methyl-4'H,6'H-spiro[cyclohexane-1,5'-furo[2,3-b]pyran]-2'(7a'H)-one (5ba) (0.038 g, 59%). TLC: R$_f$=0.4 (SiO$_2$, 20% EtOAc/hexanes); $^1$H NMR (CDCl$_3$, 500 MHz): δ 7.26-7.17 (m, 5H), 3.74-3.63 (m, 2H), 3.28 (d, J=14.1 Hz, 1H), 3.19 (d, J=14.1 Hz, 1H), 2.77 (d, J=12.5 Hz, 1H), 2.16 (d, J=12.2 Hz, 1H), 1.67 (d, J=1.5 Hz, 3H), 1.54-1.40 (m, 8H), 1.35-1.24 (m, 2H); $^{13}$C NMR (CDCl$_3$, 126 MHz): δ 171.3, 157.2, 133.5, 130.2, 128.2, 127.2, 124.8, 106.2, 72.8, 39.0, 38.8, 36.1, 34.1, 31.9, 26.1, 21.7, 21.5, 8.1; HRMS (ESI): m/z calcd for C$_{20}$H$_{24}$O$_3$Na [M+Na]$^+$ 335.1618, found 335.1611.

Example 6

3',7a'-Dimethyl-4'H,6'H-spiro[cyclopentane-1,5'-furo[2,3-b]pyran]-2'(7a'H)-one (5ca)

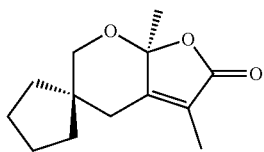

5ca

Following the General Procedure (A), to the mixture of (1-(but-3-yn-1-yl)cyclopentyl)methanol (4c) (0.02 g, 0.13 mmol), ethyl pyruvate (2a) (0.015 g, 0.13 mmol) in anhydrous (CH$_2$)$_2$Cl$_2$ (3 mL) was added AgOTf (0.002 g, 0.01 mmol) under argon atmosphere at 27° C. and stirred the reaction mixture for 4 h at 80° C. Purification of the crude product by column chromatography (SiO$_2$, 8% EtOAc/hexanes) afforded 3',7a'-dimethyl-4'H,6'H-spiro[cyclopentane-1,5'-furo[2,3-b]pyran]-2'(7a'H)-one (5ca) (0.023 g, 79%). TLC: R$_f$=0.4 (SiO$_2$, 20% EtOAc/hexanes); $^1$H NMR (CDCl$_3$, 400 MHz): δ 3.64 (d, J=11.6 Hz, 1H), 3.55 (d, J=12.2 Hz, 1H), 2.61 (d, J=12.8 Hz, 1H), 2.38 (d, J=13.4 Hz, 1H), 1.83 (s, 3H), 1.72-1.63 (m, 6H), 1.62 (s, 3H), 1.53-1.44 (m, 2H); $^{13}$C NMR (CDCl$_3$, 101 MHz): δ 171.8, 159.5, 121.8, 104.1, 72.4, 47.5, 36.1, 35.9, 34.8, 24.8, 24.5, 19.2, 8.1; HRMS (ESI): m/z calcd for C$_{13}$H$_{18}$O$_3$Na [M+Na]$^+$ 245.1148, found 245.1147.

Example 7

7a'-Methyl-3'-(1-methyl-1H-indol-3-yl)-4'H,6'H-spiro[cyclopentane-1,5'-furo[2,3-b]pyran]-2'(7a'H)-one (5cg)

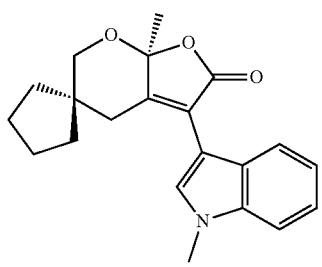

5cg

Following the General Procedure (A), to the mixture of (1-(but-3-yn-1-yl)cyclopentyl)methanol (4c) (0.1 g, 0.45 mmol), tert-butyl indoleglyoxylate (2g) (0.116 g, 0.45 mmol) in anhydrous (CH$_2$)$_2$Cl$_2$ (3 mL) was added AgOTf (0.012 g, 0.05 mmol) under argon atmosphere at 27° C. and stirred the reaction mixture for 4 h at 80° C. Purification of the crude product by column chromatography (SiO$_2$, 8% EtOAc/hexanes) afforded 7a'-methyl-3'-(1-methyl-1H-indol-3-yl)-4'H,6'H-spiro[cyclopentane-1,5'-furo[2,3-b]pyran]-2'(7a'H)-one (5cg) (0.165 g, 75%). TLC: $R_f$=0.4 (SiO$_2$, 20% EtOAc/hexanes); $^1$H NMR (CDCl$_3$, 400 MHz): δ 7.56 (s, 1H), 7.44 (d, J=7.9 Hz, 1H), 7.39 (d, J=7.9 Hz, 1H), 7.30 (d, J=6.7 Hz, 1H), 7.19 (t, J=7.9 Hz, 1H), 3.86 (s, 3H), 3.70 (d, J=11.6 Hz, 1H), 3.59 (d, J=11.6 Hz, 1H), 2.90 (d, J=11.6 Hz, 1H), 2.69 (d, J=13.4 Hz, 1H), 1.79 (s, 3H), 1.65-1.57 (m, 2H), 1.56-1.38 (m, 6H); $^{13}$C NMR (CDCl$_3$, 101 MHz): δ 170.7, 155.6, 137.0, 130.7, 125.9, 122.1, 120.1, 120.0, 119.9, 109.8, 104.1, 103.3, 72.3, 47.3, 38.0, 36.2, 34.6, 33.2, 24.8, 24.6, 20.3; HRMS (ESI): m/z calcd for C$_{21}$H$_{23}$O$_3$NNa [M+Na]$^+$ 360.1570, found 360.1562.

Example 8

3,7a-Dimethyl-5,6-dihydro-4H-furo[2,3-b]pyran-2(7aH)-one (5da)

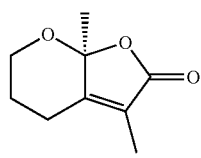

5da

Following the General Procedure (A), to the mixture of 5-hexyne-1-ol (4d) (0.1 g, 1.02 mmol), ethyl pyruvate (2a) (0.11 g, 1.02 mmol) in anhydrous (CH$_2$)$_2$Cl$_2$ (3 mL) was added AgOTf (0.025 g, 0.1 mmol) under argon atmosphere at 27° C. and stirred the reaction mixture for 4 h at 80° C. Purification of the crude product by column chromatography (SiO$_2$, 10% EtOAc/hexanes) afforded 3,7a-dimethyl-5,6-dihydro-4H-furo[2,3-b]pyran-2(7aH)-one (5da) (0.135 g, 79%). TLC: $R_f$=0.4 (SiO$_2$, 30% EtOAc/hexanes); $^1$H NMR (CDCl$_3$, 400 MHz): δ 3.93-3.86 (m, 1H), 3.78 (td, J=11.6, 2.4 Hz, 1H), 2.83-2.74 (m, 1H), 2.39 (td, J=12.2, 6.1 Hz, 1H), 1.97-1.89 (m, 1H), 1.77 (s, 3H), 1.74-1.66 (m, 1H), 1.57 (s, 3H); $^{13}$C NMR (CDCl$_3$, 101 MHz): δ 171.6, 160.1, 121.3, 104.2, 64.1, 27.3, 22.7, 20.0, 8.1; HRMS (ESI): m/z calcd for C$_9$H$_{13}$O$_3$ [M+H]$^+$ 169.0859, found 169.0859.

Example 9

7a-Dimethyl-5,6-dihydro-4H-furo[2,3-b]pyran-2(7aH)-one (5da)

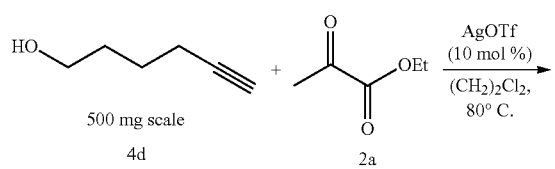

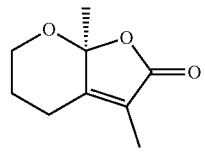

5da, 77%

To the mixture of 5-hexyne-1-ol (4d) (0.5 g, 5.09 mmol), ethyl pyruvate (2a) (0.59 g, 5.09 mmol) in anhydrous (CH$_2$)$_2$Cl$_2$ (20 mL) was added AgOTf (0.13 g, 0.509 mmol) at 27° C. under argon atmosphere and stirred the reaction mixture for 4 h at 80° C. After completion of the reaction, the reaction mixture was quenched with saturated aqueous solution of sodium bicarbonate (NaHCO$_3$) then extracted with CH$_2$Cl$_2$ (3×5 mL). The combined organic layers were dried over anhydrous sodium sulphate (Na$_2$SO$_4$) and filtered through sintered glass funnel. The residue was concentrated under reduced pressure and purified by silica gel column chromatography (100-200 mesh) (SiO$_2$, 10% EtOAc/hexanes) afforded 3,7a-dimethyl-5,6-dihydro-4H-furo[2,3-b]pyran-2(7aH)-one (5da) (0.66 g, 77%). TLC: $R_f$=0.4 (SiO$_2$, 30% EtOAc/hexanes). The product 5aa was confirmed by the comparison of its $^1$H and $^{13}$C NMR data with earlier spectra. (Copies of $^1$H and $^{13}$C NMR spectra provided in spectral section; Page No: S60).

Example 10

7a-Methyl-3-phenyl-5,6-dihydro-4H-furo[2,3-b]pyran-2(7aH)-one (5db)

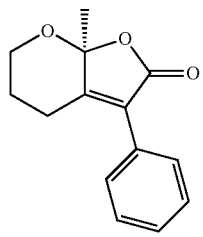

5db

Following the General Procedure (A), to the mixture of 5-hexyne-1-ol (4d) (0.1 g, 1.02 mmol), ethyl phenylglyoxylate (2b) (0.181 g, 1.02 mmol) in anhydrous (CH$_2$)$_2$Cl$_2$ (3 mL) was added AgOTf (0.025 g, 0.1 mmol) under argon atmosphere at 27° C. and stirred the reaction mixture for 4 h at 80° C. Purification of the crude product by column chromatography (SiO$_2$, 8% EtOAc/hexanes) afforded 7a-methyl-3-phenyl-5,6-dihydro-4H-furo[2,3-b]pyran-2(7aH)-one (5db) (0.106 g, 45%). TLC: $R_f$=0.2 (SiO$_2$, 30% EtOAc/hexanes); $^1$H NMR (CDCl$_3$, 500 MHz): δ 7.52-7.37 (m, 5H), 4.03-3.94 (m, 1H), 3.89 (td, J=11.0, 2.7 Hz, 1H), 3.16-3.06 (m, 1H), 2.64 (ddd, J=14.1, 11.4, 6.5 Hz, 1H), 1.96 (ddd, J=13.3, 6.5, 3.0 Hz, 1H), 1.85-1.77 (m, 1H), 1.75 (s, 3H); $^{13}$C NMR (CDCl$_3$, 126 MHz): δ 169.5, 160.7, 128.9, 128.7, 125.3, 103.8, 64.0, 27.3, 23.5, 20.6; HRMS (ESI): m/z calcd for C$_{14}$H$_{15}$O$_3$ [M+H]$^+$ 231.1016, found 231.1013.

Example 11

3-(4-Methoxyphenyl)-7a-methyl-5,6-dihydro-4H-furo[2,3-b]pyran-2(7aH)-one (5dc)

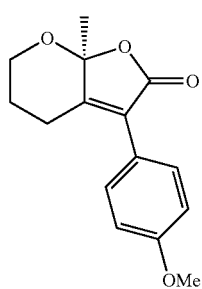

5dc

Following the General Procedure (A), to the mixture of 5-hexyne-1-ol (4d) (0.1 g, 1.02 mmol), ethyl anisylglyoxylate (2c) (0.212 g, 1.02 mmol) in anhydrous $(CH_2)_2Cl_2$ (3 mL) was added AgOTf (0.025 g, 0.1 mmol) under argon atmosphere at 27° C. and stirred the reaction mixture for 4 h at 80° C. Purification of the crude product by column chromatography ($SiO_2$, 15% EtOAc/hexanes) afforded 3-(4-methoxyphenyl)-7a-methyl-5,6-dihydro-4H-furo[2,3-b]pyran-2(7aH)-one (5dc) (0.149 g, 56%). TLC: $R_f$=0.3 ($SiO_2$, 30% EtOAc/hexanes); $^1$H NMR (CDCl$_3$, 400 MHz): δ 7.46 (d, J=8.5 Hz, 2H), 6.97 (d, J=8.5 Hz, 2H), 4.02-3.87 (m, 2H), 3.84 (s, 3H), 3.16-3.05 (m, 1H), 2.69-2.57 (m, 1H), 2.02-1.91 (m, 1H), 1.86-1.76 (m, 1H), 1.74 (s, 3H); $^{13}$C NMR (CDCl$_3$, 101 MHz): δ 169.7, 160.1, 158.9, 130.3, 124.9, 121.3, 114.1, 103.8, 64.0, 55.4, 27.1, 23.5, 20.8; HRMS (ESI): m/z calcd for $C_{15}H_{17}O_4$ [M+H]$^+$ 261.1121, found 261.1120.

Example 12

7a-Methyl-3-(4-nitrophenyl)-5,6-dihydro-4H-furo[2,3-b]pyran-2(7aH)-one (5dd)

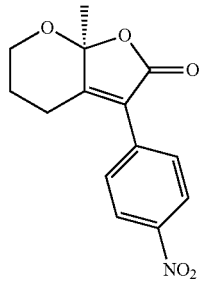

5dd

Following the General Procedure (A), to the mixture of 5-hexyne-1-ol (4d) (0.1 g, 1.02 mmol), ethyl p-nitrophenyglyoxylate (2d) (0.227 g, 1.02 mmol) in anhydrous $(CH_2)_2Cl_2$ (3 mL) was added AgOTf (0.025 g, 0.1 mmol) under argon atmosphere at 27° C. and stirred the reaction mixture for 4 h at 80° C. Purification of the crude product by column chromatography ($SiO_2$, 15% EtOAc/hexanes) afforded 7a-methyl-3-(4-nitrophenyl)-5,6-dihydro-4H-furo[2,3-b]pyran-2(7aH)-one (5dd) (0.09 g, 32%). TLC: $R_f$=0.2 ($SiO_2$, 30% EtOAc/hexanes); $^1$H NMR (CDCl$_3$, 200 MHz): δ 8.31 (d, J=9 Hz, 2H), 7.71 (d, J=9 Hz, 2H), 4.11-3.83 (m, 2H), 3.18-3.04 (m, 1H), 2.82-2.63 (m, 1H), 2.10-1.94 (m, 2H), 1.78 (s, 3H); $^{13}$C NMR (CDCl$_3$, 50 MHz): δ 163.9, 147.9, 135.4, 131.3, 129.9, 123.9, 104.1, 64.0, 27.5, 23.9, 20.4; HRMS (ESI): m/z calcd for $C_{14}H_{14}O_5N$ [M+H]$^+$ 276.0866, found 276.0864.

Example 13

7a-Methyl-3-(phenylethynyl)-5,6-dihydro-4H-furo[2,3-b]pyran-2(7aH)-one (5de)

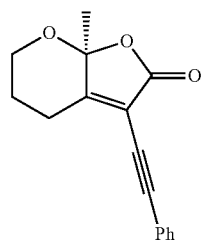

5de

Following the General Procedure (A), to the mixture of 5-hexyne-1-ol (4d) (0.1 g, 1.02 mmol), ethyl 2-oxo-4-phenylbut-3-ynoate (2e) (0.206 g, 1.02 mmol) in anhydrous $(CH_2)_2Cl_2$ (3 mL) was added AgOTf (0.025 g, 0.1 mmol) under argon atmosphere at 27° C. and stirred the reaction mixture for 4 h at 80° C. Purification of the crude product by column chromatography ($SiO_2$, 15% EtOAc/hexanes) afforded 7a-methyl-3-(phenylethynyl)-5,6-dihydro-4H-furo[2,3-b]pyran-2(7aH)-one (5de) (0.141 g, 54%). TLC: $R_f$=0.2 ($SiO_2$, 20% EtOAc/hexanes); $^1$H NMR (CDCl$_3$, 500 MHz): δ 7.55 (dd, J=7.6, 1.1 Hz, 2H), 7.41-7.32 (m, 3H), 4.00 (dt, J=12.2, 3.4 Hz, 1H), 3.85 (td, J=11.4, 3.1 Hz, 1H), 3.18-3.11 (m, 1H), 2.57 (ddd, J=13.7, 11.4, 6.5 Hz, 1H), 2.10-2.02 (m, 1H), 1.96-1.86 (m, 1H), 1.70 (s, 3H); $^{13}$C NMR (CDCl$_3$, 126 MHz): δ 167.9, 167.3, 132.0, 129.3, 128.4, 121.8, 111.3, 104.7, 98.2, 64.2, 27.8, 24.5, 20.2; HRMS (ESI): m/z calcd for $C_{16}H_{15}O_3$ [M+H]$^+$ 255.1016, found 255.1017.

Example 14

(E)-7a-Methyl-3-styryl-5,6-dihydro-4H-furo[2,3-b]pyran-2(7aH)-one (5df)

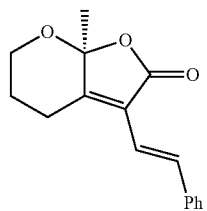

5df

Following the General Procedure (A), to the mixture of 5-hexyne-1-ol (4d) (0.1 g, 1.02 mmol), ethyl (E)-2-oxo-4-phenylbut-3-enoate (2f) (0.208 g, 1.02 mmol) in anhydrous $(CH_2)_2Cl_2$ (3 mL) was added AgOTf (0.025 g, 0.1 mmol) under argon atmosphere at 27° C. and stirred the reaction mixture for 4 h at 80° C. Purification of the crude product by column chromatography (SiO$_2$, 15% EtOAc/hexanes) afforded (E)-7a-methyl-3-styryl-5,6-dihydro-4H-furo[2,3-b]pyran-2(7aH)-one (5df) (0.09 g, 34%). TLC: R$_f$=0.3 (SiO$_2$, 30% EtOAc/hexanes); $^1$H NMR (CDCl$_3$, 500 MHz): δ 7.79 (d, J=16.4 Hz, 1H), 7.51 (d, J=7.6 Hz, 2H), 7.40-7.28 (m, 3H), 6.72 (d, J=16.0 Hz, 1H), 3.97 (dt, J=12.2, 3.4 Hz, 1H), 3.86 (td, J=11.8, 3.0 Hz, 1H), 3.14-3.07 (m, 1H), 2.60-2.51 (m, 1H), 2.08-1.99 (m, 1H), 1.89-1.80 (m, 1H), 1.69 (s, 3H); $^{13}$C NMR (CDCl$_3$, 126 MHz): δ 169.1, 159.3, 136.7, 135.4, 128.7, 128.6, 126.8, 121.5, 114.9, 103.6, 63.9, 27.5, 22.9, 20.4; HRMS (ESI): calcd for C$_1$H$_{16}$O$_3$Na [M+Na]$^+$ 279.0992, found 279.0987.

Example 15

7a-Methyl-3-(1-methyl-1H-indol-3-yl)-5,6-dihydro-4H-furo[2,3-b]pyran-2(7aH)-one (5dg)

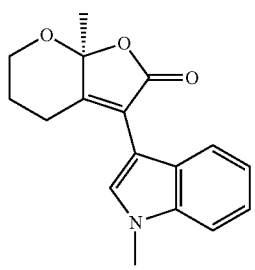

5dg

Following the General Procedure (A), to the mixture of 5-hexyne-1-ol (4d) (0.1 g, 1.02 mmol), tert-butyl indoleglyoxylate (2g) (0.264 g, 1.02 mmol) in anhydrous (CH$_2$)$_2$Cl$_2$ (3 mL) was added AgOTf (0.025 g, 0.1 mmol) under argon atmosphere at 27° C. and stirred the reaction mixture for 4 h at 80° C. Purification of the crude product by column chromatography (SiO$_2$, 20% EtOAc/hexanes) afforded 7a-methyl-3-(1-methyl-1H-indol-3-yl)-5,6-dihydro-4H-furo[2,3-b]pyran-2(7aH)-one (5dg) (0.112 g, 39%). TLC: R$_f$=0.3 (SiO$_2$, 40% EtOAc/hexanes); $^1$H NMR (CDCl$_3$, 500 MHz): δ 7.57 (s, 1H), 7.49 (d, J=8.0 Hz, 1H), 7.38 (d, J=8.0 Hz, 1H), 7.29 (t, J=7.2 Hz, 1H), 7.19 (t, J=7.6 Hz, 1H), 3.99-3.93 (m, 1H), 3.89 (dd, J=10.6, 2.7 Hz, 1H), 3.86 (s, 3H), 3.17-3.10 (m, 1H), 2.77-2.68 (m, 1H), 1.97-1.90 (m, 1H), 1.80 (s, 3H), 1.78-1.70 (m, 1H); $^{13}$C NMR (CDCl$_3$, 126 MHz): δ 170.5, 155.5, 136.9, 130.7, 126.0, 122.2, 120.1, 120.0, 109.9, 104.5, 103.4, 63.9, 33.2, 27.1, 24.5, 21.2; HRMS (ESI): calcd for C$_{17}$H$_{17}$O$_3$NNa [M+Na]$^+$ 306.1101, found 306.1094.

Example 16

7a-Methyl-3-(thiophen-2-yl)-5,6-dihydro-4H-furo[2,3-b]pyran-2(7aH)-one (5dh)

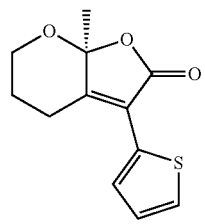

5dh

Following the General Procedure (A), to the mixture of 5-hexyne-1-ol (4d) (0.1 g, 1.02 mmol), ethyl thiophenglyoxylate (2h) (0.187 g, 1.02 mmol) in anhydrous (CH$_2$)$_2$Cl$_2$ (3 mL) was added AgOTf (0.025 g, 0.1 mmol) under argon atmosphere at 27° C. and stirred the reaction mixture for 4 h at 80° C. Purification of the crude product by column chromatography (SiO$_2$, 15% EtOAc/hexanes) afforded 7a-Methyl-3-(thiophen-2-yl)-5,6-dihydro-4H-furo[2,3-b]pyran-2(7aH)-one (5dh) (0.085 g, 35%). TLC: R$_f$=0.3 (SiO$_2$, 30% EtOAc/hexanes); $^1$H NMR (CDCl$_3$, 500 MHz): δ 7.73 (d, J=3.4 Hz, 1H), 7.44 (d, J=5.0 Hz, 1H), 7.14 (dd, J=5.0, 3.8 Hz, 1H), 4.00-3.94 (m, 1H), 3.89 (td, J=10.3, 3.0 Hz, 1H), 3.45-3.37 (m, 1H), 2.71-2.61 (m, 1H), 2.07-1.99 (m, 1H), 1.93-1.82 (m, 1H), 1.73 (s, 3H); $^{13}$C NMR (CDCl$_3$, 126 MHz): δ 168.6, 156.9, 130.5, 128.7, 127.5, 127.1, 119.2, 104.1, 64.0, 27.0, 23.9, 21.1; HRMS (ESI): m/z calcd for C$_{12}$H$_{12}$O$_3$NaS [M+Na]$^+$ 259.0399, found 259.0400.

Example 17

4a,7-Dimethyl-2,3-dihydrofuro[2,3-b][1,4]dioxin-6(4aH)-one (5ea)

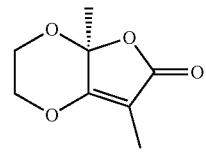

5ea

Following the General Procedure (A), to the mixture of 2-(prop-2-yn-1-yloxy)ethan-1-ol (4e) (0.1 g, 1. mmol), ethyl pyruvate (2a) (0.162 g, 1 mmol) in anhydrous (CH$_2$)$_2$Cl$_2$ (3 mL) was added AgOTf (0.025 g, 0.1 mmol) under argon atmosphere at 27° C. and stirred the reaction mixture for 4 h at 80° C. Purification of the crude product by column chromatography (SiO$_2$, 20% EtOAc/hexanes) afforded 4a,7-dimethyl-2,3-dihydrofuro[2,3-b][1,4]dioxin-6(4aH)-one (5ea) (0.065 g, 38%). TLC: R$_f$=0.3 (SiO$_2$, 40% EtOAc/hexanes); $^1$H NMR (CDCl$_3$, 400 MHz): δ 4.58-4.50 (m, 1H), 4.36 (d, J=11.6 Hz, 1H), 4.10-4.03 (m, 1H), 4.02 (d, J=1.8 Hz, 1H), 1.75 (s, 3H), 1.72 (s, 3H); $^{13}$C NMR (CDCl$_3$, 101 MHz): δ 170.7, 169.5, 103.3, 100.4, 69.5, 64.0, 27.3, 6.0; HRMS (ESI): calcd for C$_8$H$_{10}$O$_4$Na [M+Na]$^+$ 193.0471, found 193.0471.

Example 18

3,6,7a-Trimethyl-5,6-dihydro-4H-furo[2,3-b]pyran-2(7aH)-one (5fa)

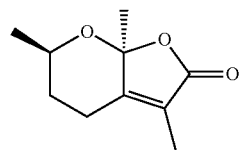

5fa

Following the General Procedure (A), to the mixture of hept-6-yn-2-ol (4f) (0.05 g, 0.45 mmol), ethyl pyruvate (2a) (0.052 g, 0.45 mmol) in anhydrous (CH$_2$)$_2$Cl$_2$ (3 mL) was added AgOTf (0.012 g, 0.05 mmol) under argon atmosphere at 27° C. and stirred the reaction mixture for 4 h at 80° C. Purification of the crude product by column chromatography (SiO$_2$, 15% EtOAc/hexanes) afforded 3,6,7a-trimethyl-5,6-dihydro-4H-furo[2,3-b]pyran-2(7aH)-one (5fa) (0.037 g, 46%). TLC: R$_f$=0.4 (SiO$_2$, 30% EtOAc/hexanes); Relative stereochemistry was assigned based on NOE analysis (see below). $^1$H NMR (CDCl$_3$, 400 MHz): δ 4.04-3.92 (m, 1H), 2.83-2.74 (m, 1H), 2.42 (td, J=13.4, 4.9 Hz, 1H), 2-1.94 (m, 1H), 1.81 (s, 3H), 1.62 (s, 3H), 1.46-1.32 (m, 1H), 1.24 (d, J=6.1 Hz, 3H); $^{13}$C NMR (CDCl$_3$, 101 MHz): δ 171.6, 160.0, 120.8, 104.0, 70.4, 35.0, 23.1, 21.1, 19.9, 8.2; HRMS (ESI): calcd for C$_{10}$H$_{14}$O$_3$Na [M+Na]$^+$ 205.0835, found 205.0833.

Example 19

Synthesis and Characterization of Furo[2,3-b]pyran-2-ones Using Tertiary Alkynols

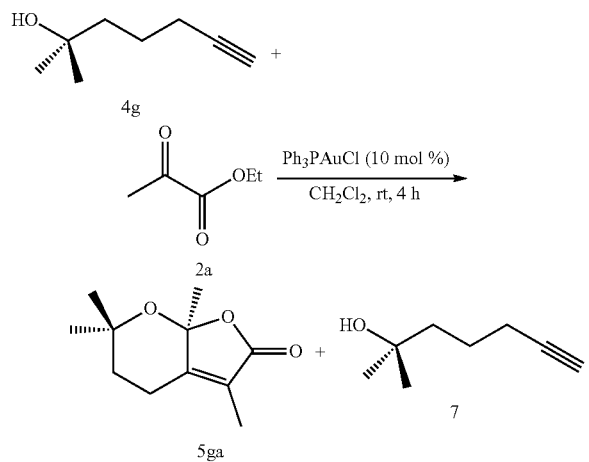

To the mixture of 2-methylhept-6-yn-2-ol (4g) (0.05 g, 0.39 mmol), ethyl pyruvate (2a) (0.046 g, 0.39 mmol) in anhydrous CH$_2$Cl$_2$ (3 mL) was added Ph$_3$PAuCl (0.019 g, 0.039 under argon atmosphere at 27° C. and stirred the reaction mixture for 4 h at 27° C. After completion of the reaction the reaction mixture was quenched with saturated aqueous solution of sodium bicarbonate (NaHCO$_3$) then extracted with CH$_2$Cl$_2$ (2×5 mL). The combined organic layers were dried over anhydrous sodium sulphate (Na$_2$SO$_4$). The residue was concentrated under reduced pressure and purified by silica gel column chromatography to afforded 3,6,6,7a-Tetramethyl-5,6-dihydro-4H-furo[2,3-b]pyran-2(7aH)-one (0.007 g, 5ga, 10%) and 6-Hydroxy-6-methylheptan-2-one (0.042 g, 7, 75%) as a colourless liquid.

5ga: TLC: R$_f$=0.4 (SiO$_2$, 20% EtOAc/hexanes); $^1$H NMR (CDCl$_3$, 400 MHz): δ 2.81-2.70 (m, 1H), 2.62-2.51 (m, 1H), 2.08-1.97 (m, 1H), 1.82 (s, 3H), 1.78-1.71 (m, 1H), 1.58 (s, 3H), 1.29 (s, 3H), 1.10 (s, 3H); $^{13}$C NMR (CDCl$_3$, 101 MHz): δ 171.3, 158.8, 123.6, 104.7, 75.9, 34.2, 30.0, 29.7, 27.4, 26.8, 19.1, 8.3; HRMS (ESI): calcd for C$_{11}$H$_{16}$O$_3$Na [M+Na]$^+$ 219.0992, found 219.0988.

7: TLC: R$_f$=0.1 (SiO$_2$, 30% EtOAc/hexanes); $^1$H NMR (CDCl$_3$, 500 MHz): δ 2.46 (t, J=7.2 Hz, 2H), 2.14 (s, 3H), 1.68-1.61 (m, 2H), 1.47-1.42 (m, 2H), 1.22 (s, 6H); $^{13}$C NMR (CDCl$_3$, 126 MHz): δ 209.1, 70.9, 43.9, 43.0, 29.9, 29.2, 18.6; HRMS (ESI): m/z calcd for C$_8$H$_{16}$O$_2$Na [M+Na]$^+$ 167.1043, found 167.1043.

Example 20

3-(4-Methoxyphenyl)-6,6,7a-trimethyl-5,6-dihydro-4H-furo[2,3-]pyran-2(7aH)-one (5gc)

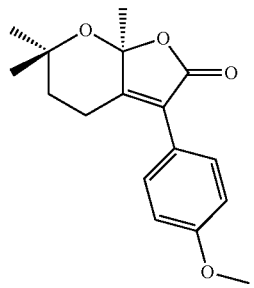

Following the General Procedure (B), to the mixture of 2-methylhept-6-yn-2-ol (4g) (0.1 g, 0.79 mmol), ethyl anisylglyoxylate (2c) (0.165 g, 0.79 mmol) in anhydrous CH$_2$Cl$_2$ (3 mL) was added Ph$_3$PAuCl (0.019 g, 0.04 mmol) and stirred the reaction mixture for 30 min then AgOTf (0.01 g, 0.04 mmol) was added under argon atmosphere at 27° C. and stirred the reaction mixture for 12 h at 27° C. Purification of the crude product by column chromatography (SiO$_2$, 5% EtOAc/hexanes) afforded 3-(4-methoxyphenyl)-6,6,7a-trimethyl-5,6-dihydro-4H-furo[2,3-b]pyran-2(7aH)-one (5gc) (0.092 g, 40%). TLC: R$_f$=0.3 (SiO$_2$, 20% EtOAc/hexanes); $^1$H NMR (CDCl$_3$, 500 MHz): δ 7.55 (d, J=8.8 Hz, 2H), 6.98 (d, J=8.8 Hz, 2H), 3.85 (s, 3H), 3.03-2.93 (m, 1H), 2.88 (ddd, J=17.1, 8.8, 3.1 Hz, 1H), 2.13-2.05 (m, 1H), 1.75 (ddd, J=14.1, 8.4, 3.4 Hz, 1H), 1.71 (s, 3H), 1.31 (s, 3H), 1.08 (s, 3H); $^{13}$C NMR (CDCl$_3$, 126 MHz): δ 169.4, 160.1, 157.3, 130.3, 126.7, 121.8, 114.1, 104.2, 75.8, 55.3, 34.0, 30.4, 27.3, 26.7, 20.8; HRMS (ESI): calcd for C$_{17}$H$_{20}$O$_4$Na [M+Na]$^+$ 311.1254, found 311.1247.

Example 21

6,6,7a-Trimethyl-3-(thiophen-2-yl)-5,6-dihydro-4H-furo[2,3-b]pyran-2(7aH)-one (5gh)

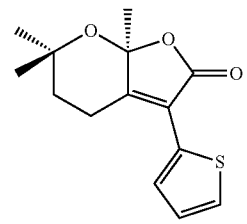

Following the General Procedure (B), to the mixture of 2-methylhept-6-yn-2-ol (4g) (0.05 g, 0.4 mmol), ethyl thiophene glyoxylate (2h) (0.073 g, 0.4 mmol) in anhydrous CH$_2$Cl$_2$ (3 mL) was added Ph$_3$PAuCl (0.009 g, 0.02 mmol) and stirred the reaction mixture for 30 min then AgOTf (0.005 g, 0.02 mmol) was added under argon atmosphere at 27° C. and stirred the reaction mixture for 12 h at 27° C.

Purification of the crude product by column chromatography (SiO$_2$, 5% EtOAc/hexanes) afforded 6,6,7a-trimethyl-3-(thiophen-2-yl)-5,6-dihydro-4H-furo[2,3-b]pyran-2(7aH)-one (5gh) (0.036 g, 35%). TLC: R$_f$=0.4 (SiO$_2$, 20% EtOAc/hexanes); $^1$H NMR (CDCl$_3$, 500 MHz): δ 7.73 (d, J=3.8 Hz, 1H), 7.48 (d, J=4.6 Hz, 1H), 7.17 (dd, J=5.0, 3.8 Hz, 1H), 3.28-3.17 (m, 1H), 2.88 (ddd, J=17.9, 8.7, 2.6 Hz, 1H), 2.19-2.10 (m, 1H), 1.84 (ddd, J=14.5, 8.4, 2.6 Hz, 1H), 1.70 (s, 3H), 1.33 (s, 3H), 1.10 (s, 3H); $^{13}$C NMR (CDCl$_3$, 126 MHz): δ 168.3, 155.4, 131.0, 128.5, 127.6, 121.2, 104.6, 76.0, 33.6, 30.5, 27.8, 26.5, 21.1; HRMS (ESI): m/z calcd for C$_{14}$H$_{16}$O$_3$NaS [M+Na]$^+$ 287.0712, found 287.0707.

ADVANTAGES OF THE INVENTION

Novel furo[2,3-b]pyran-2-one compounds.
One step process of synthesis using mild Lewis acids.
Commercially available/readily accessible starting materials used.
Products in excellent yield.
Compounds useful for synthesis of furo[2,3-b]pyran-2-one derived bio-active natural products.

We claim:
1. A furo[2,3-b]pyran-2-one compound of formula (I),

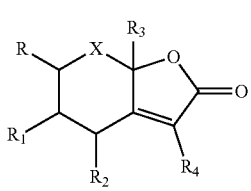

Formula (I)

wherein, R, R$_1$, and R$_2$ are independently selected from the group consisting of hydrogen, C$_1$-C$_6$ alkyl and C$_1$-C$_6$ cycloalkyl;
R$_3$ is selected from the group consisting of C$_1$-C$_7$ alkyl and C$_6$ aryl;
R$_4$ is selected from the group consisting of hydrogen, C$_1$-C$_7$ alkyl, C$_4$-C$_8$ aryl, C$_4$-C$_8$ hetero aryl, alkynyl, substituted alkynyl, alkenyl and substituted alkenyl; and
X is selected from the group consisting of O, NH and S.

2. The compound as claimed in claim 1, wherein said compound of formula (I) is selected from the groups consisting of:
3',7a'-Dimethyl-4'H,6'H-spiro[cyclohexane-1,5'-furo[2,3-b]pyran]-2'(7a'H) one,
7a'-Methyl-3'-phenyl-4'H,6'H-spiro[cyclohexane-1,5'-furo[2,3-b]pyran]-2'(7a'H)-one,
3'-(4-Methoxyphenyl)-7a'-methyl-4'H,6'H-spiro[cyclohexane-1,5'-furo[2,3-b]pyran]-2'(7a'H)-one,
7a'-Methyl-3'-(4-nitrophenyl)-4'H,6'H-spiro[cyclohexane-1,5'-furo[2,3-b]pyran]-2'(7a'H)-one,
7a'-Benzyl-3'-methyl-4'H,6'H-spiro[cyclohexane-1,5'-furo[2,3-b]pyran]-2'(7a'H)-one,
3',7a'-Dimethyl-4'H,6'H-spiro[cyclopentane-1,5'-furo[2,3-b]pyran]-2'(7a'H)-one,
7a'-Methyl-3'-(1-methyl-1H-indol-3-yl)-4'H,6'H-spiro[cyclopentane-1,5'-furo[2,3-b]pyran]-2'(7a'H)-one,
3,7a-Dimethyl-5,6-dihydro-4H-furo[2,3-b]pyran-2(7aH)-one,
7a-Methyl-3-phenyl-5,6-dihydro-4H-furo[2,3-b]pyran-2(7aH)-one,
3-(4-Methoxyphenyl)-7a-methyl-5,6-dihydro-4H-furo[2,3-b]pyran-2(7aH)-one,
7a-Methyl-3-(4-nitrophenyl)-5,6-dihydro-4H-furo[2,3-b]pyran-2(7aH)-one,
7a-Methyl-3-(phenylethynyl)-5,6-dihydro-4H-furo[2,3-b]pyran-2(7aH)-one,
(E)-7a-Methyl-3-styryl-5,6-dihydro-4H-furo[2,3-b]pyran-2(7aH)-one,
7a-Methyl-3-(1-methyl-1H-indol-3-yl)-5,6-dihydro-4H-furo[2,3-b]pyran-2(7aH)-one,
7a-Methyl-3-(thiophen-2-yl)-5,6-dihydro-4H-furo[2,3-b]pyran-2(7aH)-one,
4a,7-Dimethyl-2,3-dihydrofuro[2,3-b][1,4]dioxin-6(4aH)-one,
3,6,7a-Trimethyl-5,6-dihydro-4H-furo[2,3-b]pyran-2(7aH)-one,
3,6,6,7a-Tetramethyl-5,6-dihydro-4H-furo[2,3-b]pyran-2(7aH)-one,
3-(4-Methoxyphenyl)-6,6,7a-trimethyl-5,6-dihydro-4H-furo[2,3-b]pyran-2(7aH)-one, and
6,6,7a-Trimethyl-3-(thiophen-2-yl)-5,6-dihydro-4H-furo[2,3-b]pyran-2(7aH)-one.

3. A single step process for preparation of furo[2,3-b]pyran-2-one compound of formula (I) as claimed in claim 1, comprising the step of reacting an alkynol of formula (III)

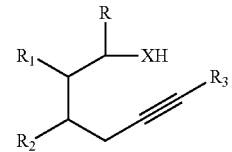

III wherein, R, R$_1$ and R$_2$ are independently selected from the group consisting of hydrogen, C$_1$-C$_6$ alkyl and C$_1$-C$_6$ cycloalkyl;
R$_3$ is selected from the group consisting of hydrogen and C$_6$ aryl; and
X is selected from the group consisting of O, NH and S, and an α-ketoester of formula (II)

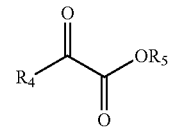

II wherein, R$_4$ is selected from the group consisting of hydrogen, C$_1$-C$_7$ alkyl, C$_4$-C$_8$ aryl, C$_4$-C$_8$ hetero aryl, alkynyl, substituted alkynyl, alkenyl, and substituted alkenyl; and
R$_5$ is selected from the group consisting of C$_2$-C$_4$ alkyl, in presence of a Lewis acid catalyst to obtain the corresponding furo[2,3-b]pyran-2-one compound of formula (I).

4. The process as claimed in claim 3, wherein said alkynol is selected from the group consisting of (1-(but-3-yn-1-yl)cyclohexyl)methanol, (1-(4-phenylbut-3-yn-1-yl)cyclohexyl)methanol, (1-(but-3-yn-1-yl)cyclopentyl)methanol, 5-hexyne-1-ol, 2-(prop-2-yn-1-yloxy)ethanl-ol, hept-6-yn-2-ol and 2-methylhept-6-yn-2-ol.

5. The process as claimed in claim 3, wherein said α-ketoester is selected from the group consisting of ethyl pyruvate, ethyl phenylglyoxylate, ethyl anisylglyoxylate, ethyl p-nitrophenyglyoxylate, ethyl 2-oxo-4-phenylbut-3-ynoate, ethyl (E)-2-oxo-4-phenylbut-3-enoate, tert-butyl indoleglyoxylate and ethyl thiophene glyoxylate.

6. The process as claimed in claim 3, wherein said Lewis acid catalyst is selected from the group consisting of $Hg(OTf)_2$, AgOTf, $Bi(OTf)_3$, $In(OTf)_3$, $BF_3OEti/Bi(OTf)_3$, $TFA/(BiOTf)_3$, $AgOTf/PPh_3PAuCl$, $Cu(OTf)_2$, $Sc(OTf)_3$, $Bi(OTf)_3$, $Bi(OTf)_3$ and FeCh or any mixture thereof.

7. The process as claimed in claim 3, wherein said process is carried out at temperature in the range of 25 to 100° C. for a time period in the range of 4 hrs to 12 hrs.

8. A pharmaceutical composition comprising a compound according to claim 1, or a stereoisomer, or ester or pharmaceutically acceptable salt thereof, and a pharmaceutically acceptable carrier, diluent or excipient.

\* \* \* \* \*